US 11,400,264 B2

(12) United States Patent
Yoshino

(10) Patent No.: US 11,400,264 B2
(45) Date of Patent: Aug. 2, 2022

(54) TREATMENT SYSTEM AND METHOD FOR ENLARGING NARROW PORTION

(71) Applicant: OLYMPUS CORPORATION, Tokyo (JP)

(72) Inventor: Masahiro Yoshino, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 183 days.

(21) Appl. No.: 16/839,297

(22) Filed: Apr. 3, 2020

(65) Prior Publication Data

US 2020/0230383 A1 Jul. 23, 2020

Related U.S. Application Data

(63) Continuation of application No. PCT/JP2017/036712, filed on Oct. 10, 2017.

(51) Int. Cl.
*A61M 29/00* (2006.01)
*A61M 25/02* (2006.01)
(Continued)

(52) U.S. Cl.
CPC ............ *A61M 29/00* (2013.01); *A61M 25/02* (2013.01); *A61M 25/09* (2013.01); *A61M 2025/0293* (2013.01); *A61M 2025/09008* (2013.01); *A61M 2029/025* (2013.01); *A61M 2205/0216* (2013.01); *A61M 2210/0618* (2013.01)

(58) Field of Classification Search
CPC ........... A61M 2025/0293; A61M 2025/09008; A61M 29/00; A61M 29/02
See application file for complete search history.

(56) References Cited

U.S. PATENT DOCUMENTS 4,230,109 A * 10/1980 Geiss ................. A61M 39/1011
285/114
6,488,653 B1 * 12/2002 Lombardo ........ A61M 25/1002
604/103.06

(Continued)

FOREIGN PATENT DOCUMENTS

JP    2008-513125 A    5/2008
JP    2008-295729 A    12/2008

OTHER PUBLICATIONS

International Search Report dated Jan. 9, 2018 issued in International Application No. PCT/JP2017/036712.

(Continued)

*Primary Examiner* — Deanna K Hall
(74) *Attorney, Agent, or Firm* — Scully, Scott, Murphy & Presser, P.C.

(57) ABSTRACT

A treatment system includes a guide, tubular dilator members, an operation portion, and a holding portion. The guide extends linearly or curvilinearly. The dilator members pass the guide inside and are configured to move forward along the guide. The operation portion is configured to sequentially move the plurality of dilator members from a proximal end side of the guide to a distal end side of the guide. The holding portion is provided on the guide. A distance between outer edges of the holding portion in a direction intersecting a direction from the proximal end side toward the distal end side of the guide is larger or is configured to be larger than a distance between outer edges of the guide.

20 Claims, 11 Drawing Sheets

(51) Int. Cl.
*A61M 25/09* (2006.01)
*A61M 29/02* (2006.01)

(56) References Cited

U.S. PATENT DOCUMENTS

2010/0274275 A1    10/2010   Stammberger et al.
2017/0000981 A1     1/2017   Gerrans et al.
2017/0000990 A1 *   1/2017   Gerrans ............ A61B 1/00105

OTHER PUBLICATIONS

English translation of International Preliminary Report on Patentability dated Apr. 14, 2020, together with the Written Opinion received in related International Application No. PCT/JP2017/036712.

* cited by examiner

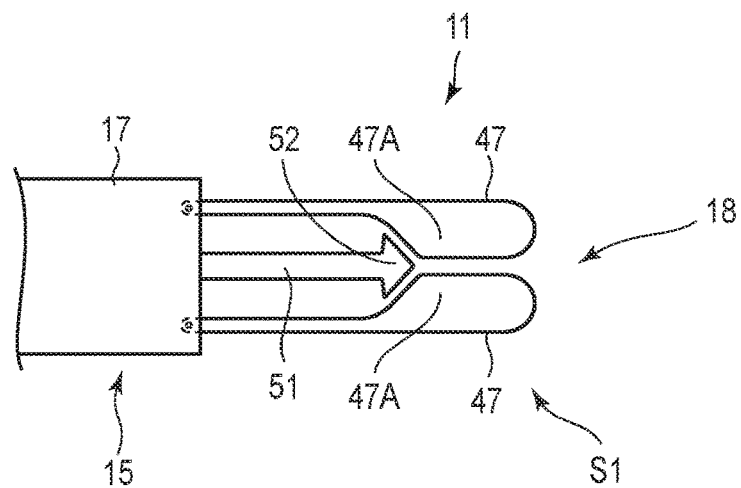
F I G. 14
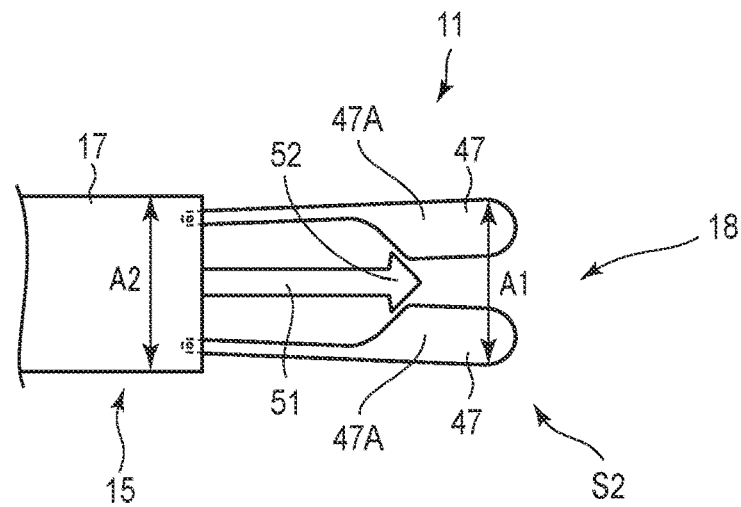
F I G. 15
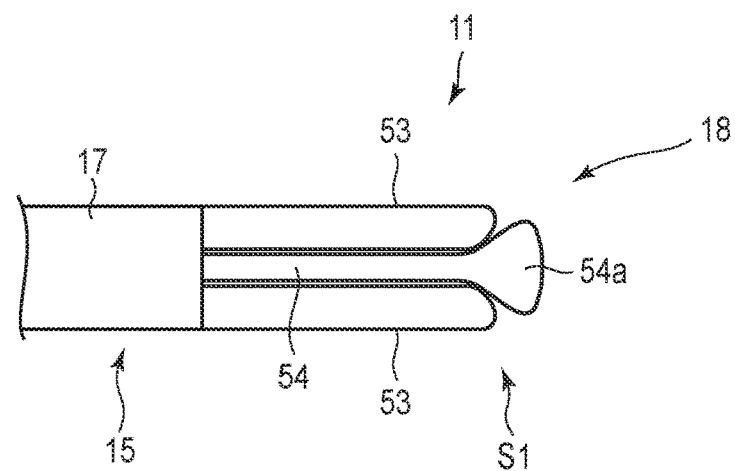
F I G. 16

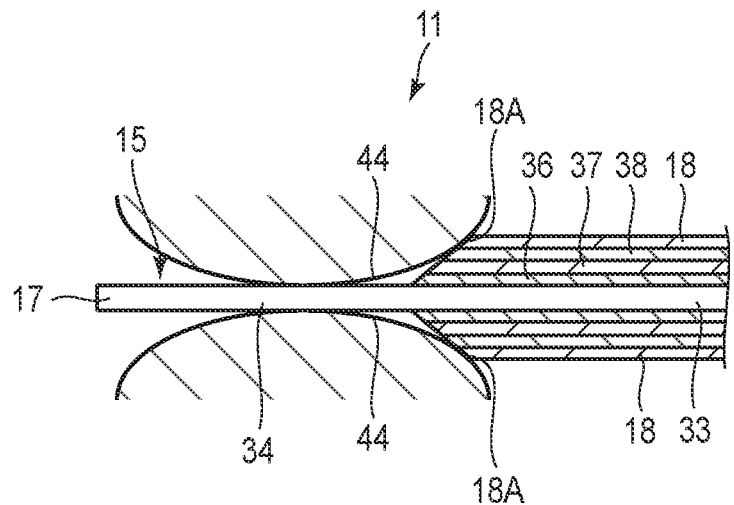
F I G. 21
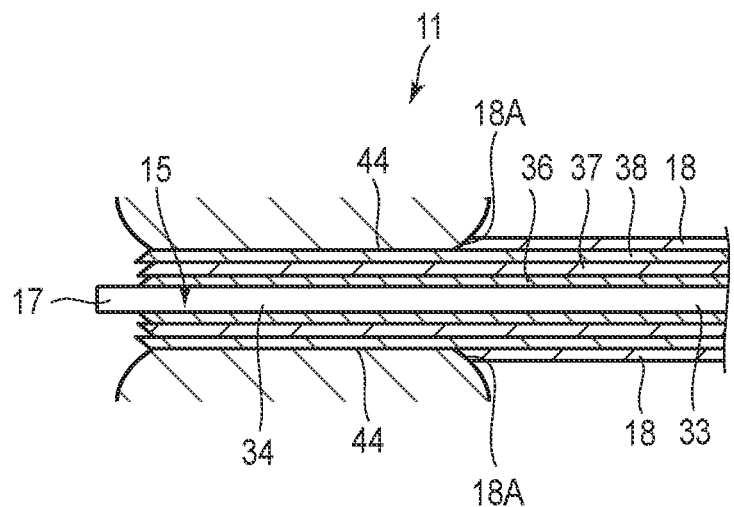
F I G. 22

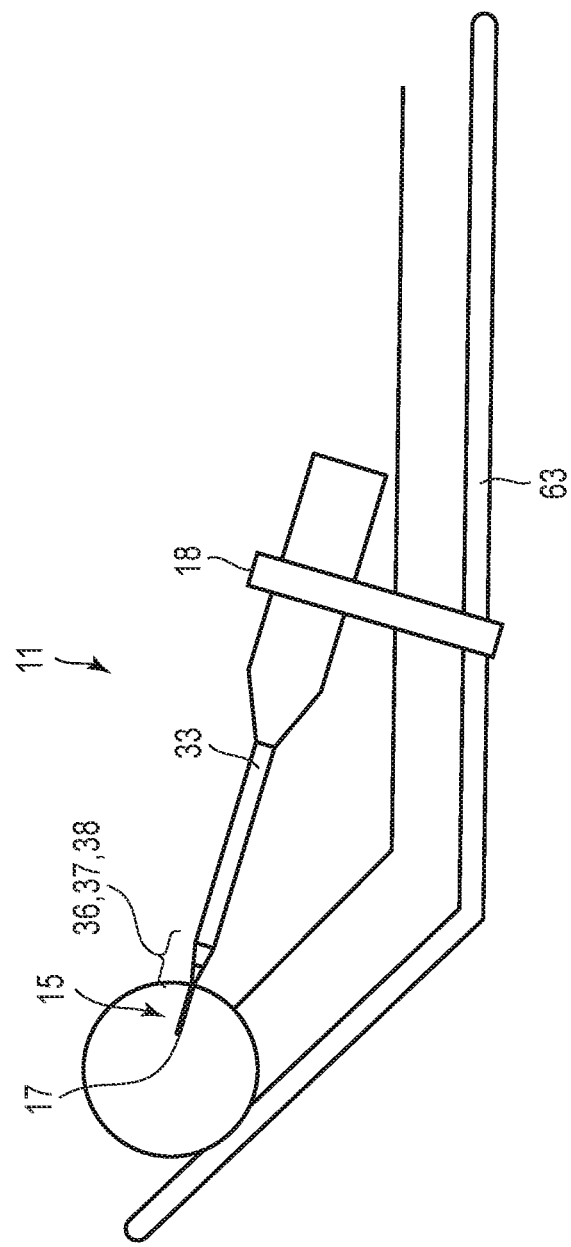

TREATMENT SYSTEM AND METHOD FOR ENLARGING NARROW PORTION

CROSS-REFERENCE TO RELATED APPLICATIONS

This application is a Continuation Application of PCT Application No. PCT/JP2017/036712, filed Oct. 10, 2017, the entire contents of which are incorporated herein by reference.

FIELD

The present invention relates to a treatment system and a method for enlarging a narrow portion.

BACKGROUND

For example, U.S. Patent Application Publication No. 2017/0000981 and U.S. Patent Application Publication No. 2017/0000990 disclose devices for expanding a constricted area of a paranasal sinus by sequentially inserting a plurality of tapered pipes having different outer diameters.

SUMMARY

According to one aspect of the present invention, a treatment system includes a guide, a plurality of tubular dilator members, an operation portion, and a holding portion. The guide extends linearly or curvilinearly from a proximal end portion to a distal end portion. The plurality of tubular dilator members pass the guide inside and are configured to move forward along the guide. The operation portion is configured to sequentially move the plurality of dilator members from a side of the proximal end portion to a side of the distal end portion. The holding portion is provided on the guide. A distance between outer edges of the holding portion in a direction intersecting a direction from the side of the proximal end portion toward the side of the distal end portion of the guide is larger or is configured to be larger than a distance between outer edges of the guide.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 14 is a schematic diagram illustrating the holding portion in the first state in the treatment system according to a third modification of the first embodiment.

FIG. 15 is a schematic diagram illustrating a state in which the diameter of the holding portion illustrated in FIG. 14 is increased to the second state.

FIG. 16 is a schematic diagram illustrating the holding portion in the first state in the treatment system according to a fourth modification of the first embodiment.

FIG. 21 is a cross-sectional view showing a configuration of a guide, first to third dilator members, and a holding portion in a treatment system according to a third embodiment.

FIG. 22 is a cross-sectional view showing a state after all of the first to third dilator members in the treatment system shown in FIG. 21 have been inserted into a narrow portion.

FIG. 24 is a cross-sectional view showing a configuration of a guide, first to third dilator members, and a holding portion in a treatment system according to a fifth embodiment.

DETAILED DESCRIPTION

First Embodiment

Hereinafter, a first embodiment of a treatment system 11 will be described with reference to FIGS. 1 to 9.

Figure 1:
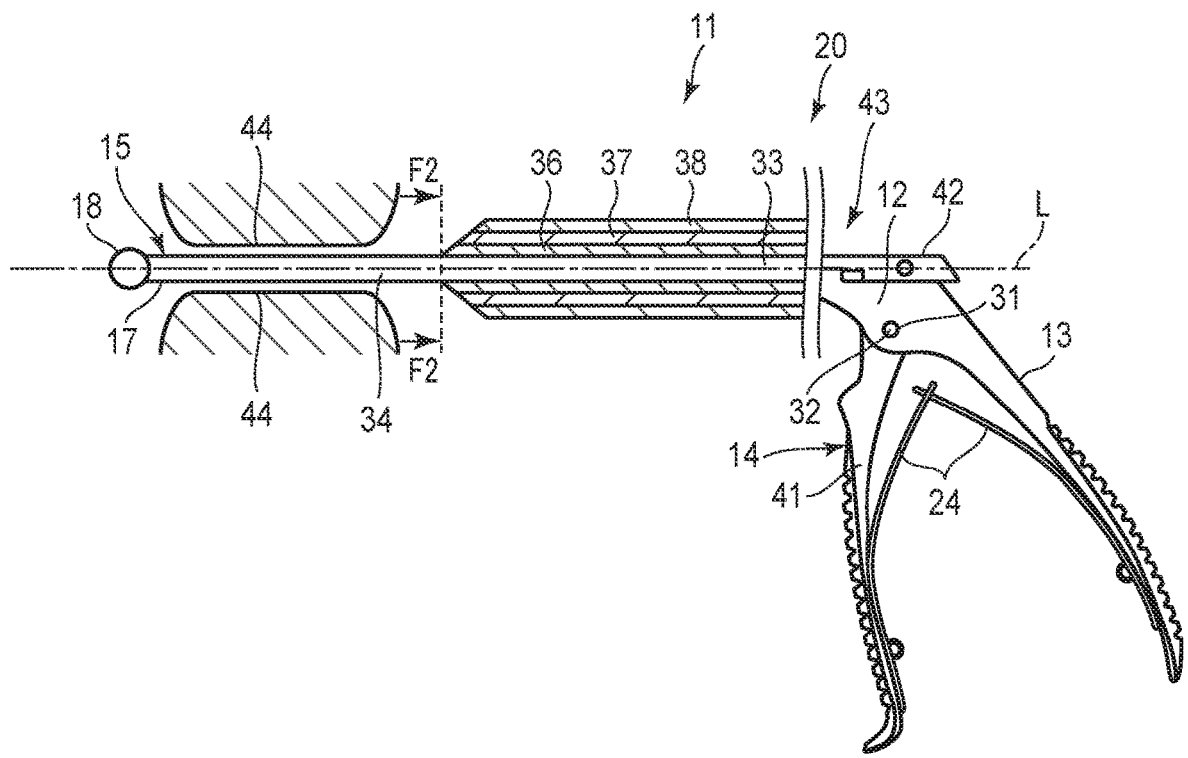
FIG. 1 is a schematic diagram showing an overall configuration of a treatment system according to a first embodiment, and showing first to third dilator members on a section cut along a plane passing through a longitudinal axis of a guide.
Figure 2:
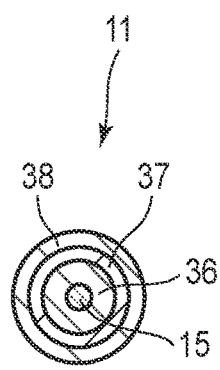
FIG. 2 is a cross-sectional view taken along line F2-F2 shown in FIG. 1.
Figure 4:
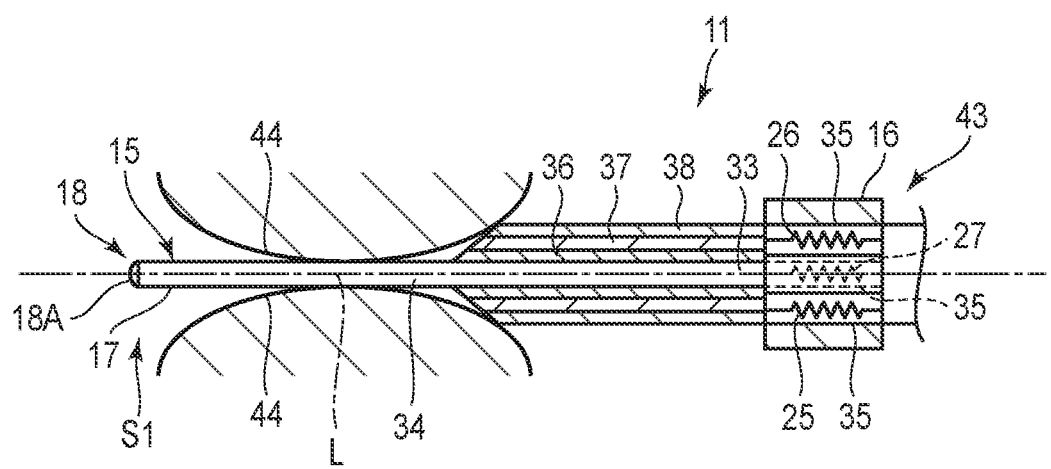
FIG. 4 is a cross-sectional view showing the guide, the first to third dilator members, a cylinder, a holding portion, and first to third spring members of the treatment system shown in FIG. 1.

The treatment system 11 of the present embodiment is mainly inserted into a narrow portion (constricted area) 44 of a human body, for example, the narrow portion 44 formed at a boundary between a paranasal sinus and a nasal cavity and used for a treatment of expanding the narrow portion. As shown in FIGS. 1 and 4, the treatment system 11 includes a main body 12, a fixed handle portion 13 extending from the main body 12, a movable handle portion 14 rotatable with respect to the main body 12, a guide 15 linearly or curvilinearly extending from the main body 12, first to third dilator members 36, 37, and 38 that are cylindrical and provided outside the guide 15, a cylindrical cylinder 16 rotatably provided around the guide 15, a holding portion 18 fixed to a distal end portion 17 of the guide 15, a leaf spring portion 24 (spring portion) interposed between the fixed handle portion 13 and the movable handle portion 14, and first to third spring members (elastic members) 25, 26, and 27 incorporated in the cylinder 16 to advance the first to third dilator members 36, 37, and 38. The main body 12 includes a hole 31. The movable handle portion 14 has a rotation shaft 32 that fits inside the hole 31 of the movable handle portion 14, and is configured to rotate with respect to the main body 12 around the hole 31 (rotation axis 32).

Figure 3:
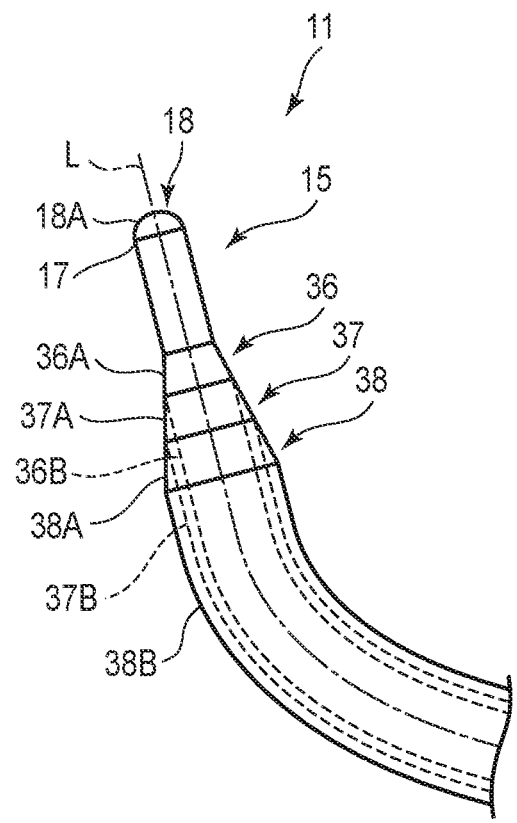
FIG. 3 is a side view showing the first to third dilator members of the treatment system shown in FIG. 1.

The guide 15 includes a distal end portion 17, a proximal end portion 33 opposite to the distal end portion 17, and an intermediate portion 34 connecting the distal end portion 17 and the proximal end portion 33. The guide 15 extends linearly or curvilinearly from the proximal end portion 33 to the distal end portion 17. The longitudinal axis L of the guide 15 is defined as an axis (center axis) connecting the distal end portion 17 and the proximal end portion 33. The distal end portion 33 is fixed to the main body 12. As shown in FIG. 3, in reality, the guide 15 is bent in an arc shape, so as to follow the bending shape of the nasal cavity and the paranasal sinuses (particularly, the frontal sinus or the maxillary sinus) of the patient. However, FIG. 1 schematically illustrates the guide 15 as being straight. The leaf spring portion 24 can bias the movable handle portion 14 in a direction away from the fixed handle portion 13.

As shown in FIG. 4, the cylinder 16 is formed as a revolver of a rotary pistol or a column having a lotus root-like cross section. The cylinder 16 has a plurality of (for example, three) through holes 35, a second through hole provided at a central portion, through which the guide is passed, and a plurality of (for example, three) holding levers. The holding levers are respectively provided adjacent to the through holes 35. Each of the holding levers is configured to hold any one of the first to third spring members 25, 26, and 27 in a compressed state.

The plurality of through holes 35 are, for example, uniformly arranged at 120° intervals around the center axis of the cylinder 16. The center axis of the cylinder 16 coincides with a longitudinal axis L of the guide 15. The first spring member 25 is housed inside one through hole 35, the second spring member 26 is housed inside another through hole 35, and the third spring member 27 is housed inside the other through holes 35.

The first to third dilator members 36, 37, and 38 pass the guide 15 inside, and are configured to move forward and backward along the guide 15. The first dilator member 36 is located at the innermost position and is provided at a position adjacent to the guide 15. The second dilator member 37 is provided at a position outside the first dilator member 36. The third dilator member 38 is provided at a position outside the second dilator member 37. Thus, the first to third dilator members 36, 37, and 38 are arranged concentrically. The first to third dilator members 36, 37, and 38 are arranged on a side of the proximal end portion 33 of the guide 15 in an initial state. The number of dilator members is not limited to three, and may be, for example, two or four or more. The first dilator member 36 is an example of a first member, and the second dilator member 37 is an example of a second member.

The first dilator member 36 is configured to move forward and backward along the longitudinal axis L of the guide 15. As shown in FIG. 3, the first dilator member 36 has a first rigid portion 36A provided on a side of the distal end portion 17 and a first flexible portion 36B provided on the side of the proximal end portion 33. In the present embodiment, the outer peripheral surface of the first rigid portion 36A is formed in a tapered shape in which the diameter decreases, for example, toward the distal end portion 17. The first rigid portion 36A is formed of a rigid material, for example, a metal material. The first rigid portion 36A is an example of a tapered portion that tapers toward the distal end portion 17. The first flexible portion 36B is formed, for example, in a cylindrical shape. The first flexible portion 36B is formed of a flexible material, for example, a resin material or the like. By providing the first flexible portion 36B in this manner, the first dilator member 36 can be moved forward and backward along the curved guide 15.

The second dilator member 37 is configured to move forward and backward along the guide 15. The second dilator member 37 has a second rigid portion 37A provided on the side of the distal end portion 17 and a second flexible portion 37B provided on the side of the proximal end portion 33. In the present embodiment, the outer peripheral surface of the second rigid portion 37A is formed in a tapered shape in which the diameter decreases, for example, toward the distal end portion 17. The second rigid portion 37A is formed of a rigid material, for example, a metal material. The second rigid portion 37A is an example of a tapered portion that tapers toward the distal end portion 17. The second flexible portion 37B is formed, for example, in a cylindrical shape. The second flexible portion 37B is formed of a flexible material, for example, a resin material or the like.

The third dilator member 38 is configured to move forward and backward along the guide 15. The third dilator member 38 has a third rigid portion 38A provided on the side of the distal end portion 17 and a third flexible portion 38B provided on the side of the proximal end portion 33. In the present embodiment, the outer peripheral surface of the third rigid portion 38A is formed in a tapered shape in which the diameter decreases, for example, toward the distal end portion 17. The third rigid portion 38A is formed of a rigid material, for example, a metal material. The third rigid portion 38A is an example of a tapered portion that tapers toward the distal end portion 17. The third flexible portion 38B is formed, for example, in a cylindrical shape. The third flexible portion 38B is formed of a flexible material, for example, a resin material or the like.

As shown in FIG. 4, the first spring member 25 is interposed between the first dilator member 36 and the movable handle portion 14 in a compressed state. The second spring member 26 is interposed between the second dilator member 37 and the movable handle portion 14 in a compressed state. The third spring member 27 is interposed between the third dilator member 38 and the movable handle portion 14 in a compressed state.

As shown in FIG. 1, the movable handle portion 14 includes a movable handle main body 41, a release member 42 that is in contact with the holding levers and configured to release the compressed state of the first to third spring members 25, 26, and 27, and a conversion mechanism 43 that converts a rotational movement of the movable handle main body 41 about the rotation axis into a rotational movement that rotates the cylinder 16 clockwise. The release member 42 is configured to release the compressed state of the first to third spring members 25, 26, and 27 by rotating the holding levers by abutting the respective holding levers. The first to third spring members 25, 26, and 27 whose compression state has been released can apply the repulsive force to the first to third dilator members 36, 37, and 38.

The movable handle portion 14 is grasped by the user, rotated toward the fixed handle portion 13, and brought into contact with the fixed handle portion 13, whereby the repulsive forces of the first to third spring members 25, 26, and 27 can be released one by one in order. More specifically, the movable handle portion 14 can release the repulsive force of the first spring member 25 when the movable handle portion 14 is grasped by the user and brought into contact with the fixed handle portion 13 for the first time. The movable handle portion 14 can release the repulsive force of the second spring member 26 when the movable handle portion 14 is grasped by the user and brought into contact with the fixed handle portion 13 for the second time. The movable handle portion 14 can release the repulsive force of the third spring member 27 when the movable handle portion 14 is grasped by the user and brought into contact with the fixed handle portion 13 for the third time.

The conversion mechanism 43 includes a cam mechanism. The cam mechanism is configured to convert a back-and-forth movement of the movable handle portion 14 in the vicinity of the rotation axis 32 into a rotational movement for rotating the cylinder 16 clockwise by 120° when the movable handle portion 14 returns from the state of abutting the fixed handle portion 13 to the initial position by the repulsive force of the leaf spring portion 24. A well-known structure can be used as the conversion mechanism 43 (cam mechanism). For example, the conversion mechanism 43 (cam mechanism) may include an inclined surface provided on the cylinder 16, and a prism-shaped contact piece provided on the movable handle portion 14 side and configured to abut the inclined surface at its distal end to rotate the cylinder 16. The movable handle portion 14 and the first to third spring members 25, 26, and 27 are an example of an operation portion 20 configured to sequentially move the first to third dilator members 36, 37, and 38 from the side of the proximal end portion 33 to the side of the distal end portion 17 and insert the first to third dilator members 36, 37, and 38 into the narrow portion 44.

Figure 5:
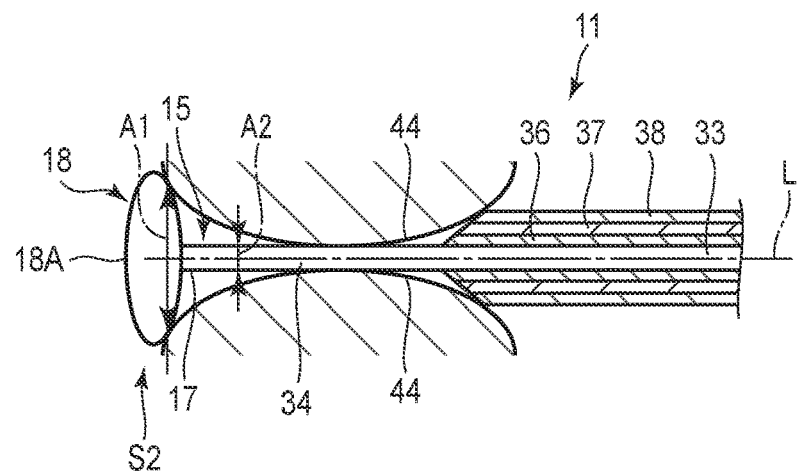
FIG. 5 is a cross-sectional view showing a state after the holding portion is expanded from a first state to a second state in the treatment system shown in FIG. 4.

As shown in FIGS. 4 and 5, in the present embodiment, the holding portion 18 includes a distal end engagement portion provided on the side of the distal end portion 17 of the guide 15. The holding portion 18 (distal end engagement portion) comprises a balloon-shaped member 18A. The balloon-shaped member 18A comprises a balloon formed of a rubbery elastic material. The balloon-shaped member 18A can be suitably formed of a rubber material or the like. The holding portion 18 can be inflatable and deflatable. The holding portion 18 can be deformed between a first state S1 having a diameter (distance between outer edges in a direction intersecting the longitudinal axis direction) equivalent to the diameter (inner diameter, distance between inner walls) of the narrow portion 44 located at the boundary between a paranasal sinus and a nasal cavity, and a second state S2 having a larger diameter (distance between outer edges) than the first state S1.

Subsequently, with reference to FIGS. 4 to 9, a treatment for enlarging the narrow portion 44 using the treatment system 11 of the present embodiment will be described. As shown in FIG. 4, the operator inserts the guide 15 into the narrow portion 44 of the human body, for example, a boundary between a paranasal sinus and a nasal cavity. The narrow portion 44 is located at the entrance of the paranasal sinus, and forms a passage communicating with the paranasal sinus and the nasal cavity. The operator inserts the guide 15 through the external naris and positions the guide 15 in the paranasal sinus, for example in the frontal sinus or maxillary sinus. At this time, the guide 15 is inserted into the narrow portion 44 until the distal end portion 17 of the guide 15 is positioned deeper than the narrow portion 44.

Figure 6:
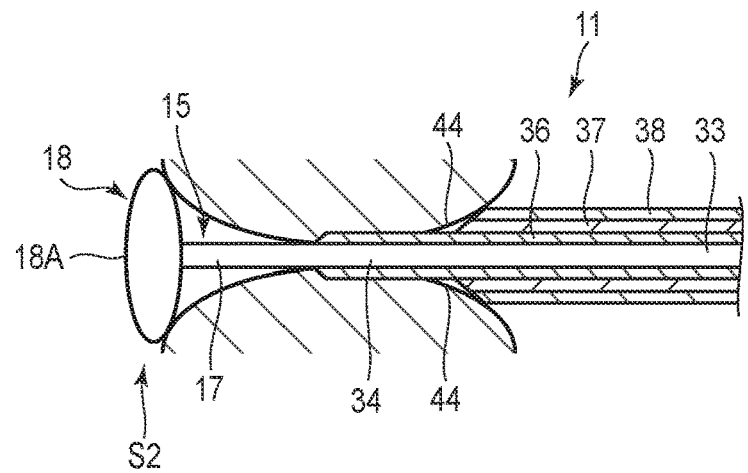
FIG. 6 is a cross-sectional view showing a state in which the first dilator member is being advanced from the proximal end toward the distal end in the treatment system shown in FIG. 5.

The operator inflates the holding portion 18 from the first state S1 shown in FIG. 4 to the second state S2 shown in FIG. 5, for example, by sending a fluid, such as air or water, to the holding portion 18 (balloon-shaped member 18A) through the tubular guide 15. At this time, the distance between the outer edges of the balloon-like member 18A orthogonal to the longitudinal axis L of the guide 15 (or the inner cross-sectional area) indicated by the reference symbol A1 in FIG. 5 is larger than the distance between the outer edges of the distal end portion 17 of the guide 15 (or the inner cross-sectional area) indicated by the reference symbol A2 in FIG. 5. As a result, the holding portion 18 engages with the deep portion of the narrow portion 44. Accordingly, the position of the guide 15 can be fixed with respect to the narrow portion 44 so that the guide 15 does not retract. In this state, the operator grasps the movable handle 14 to release the first spring member 25 from the compressed state, and causes the repulsive force of the first spring member 25 to act on the first dilator member 36. As a result, as shown in FIG. 6, the first dilator member 36 moves forward from the proximal end portion 33 to the distal end portion 17 and is inserted into the narrow portion 44. By inserting the first dilator member 36 into the narrow portion 44, the diameter (inner diameter) of the narrow portion 44 is increased. When the first dilator member 36 moves forward in this way, a reaction force is generated in a direction opposite to the direction in which the first dilator member 36 moves forward, and the reaction force acts on the first dilator member 36 and the guide 15 to push them backward. However, in this embodiment, since the guide 15 can be fixed by the balloon-shaped member 18A (holding portion 18) provided at the distal end portion 17 of the guide 15, the reaction force can be received by the balloon-shaped member 18A. Therefore, the first dilator member 36 and the guide 15 are prevented from retracting in the direction from the distal end portion 17 toward the proximal end portion 33 due to the reaction force.

When the operator releases the grasp on the movable handle 14 after the insertion of the first dilator member 36 into the narrow portion 44 is completed, the movable handle portion 14 returns to the initial position by the action of the leaf spring portion 24. At this time, the linear motion of the movable handle portion 14 in the vicinity of the rotation axis 32 is converted into a motion for rotating the cylinder 16 in the clockwise direction via the conversion mechanism (cam mechanism) 43. The return operation of the movable handle portion 14 causes the cylinder 16 to rotate, for example, 120° in the clockwise direction. The rotation direction of the cylinder 16 may be the counterclockwise direction.

When the operator grasps the movable handle 14 to release the second spring member 26 from the compressed state, the repulsive force of the second spring member 26 is caused to act on the second dilator member 37. As a result, the second dilator member 37 moves forward from the proximal end portion 33 to the distal end portion 17 and is inserted into the narrow portion 44 and outside the first dilator member 36. By inserting the second dilator member 37 into the narrow portion 44, the diameter (inner diameter) of the narrow portion 44 is further increased. At this time, similarly, a reaction force is generated in the direction opposite to the direction in which the second dilator member 37 moves forward; however, the reaction force is received by the balloon-shaped member 18A (holding portion 18) provided in the distal portion 17 of the guide 15.

When the operator releases the grasp on the movable handle 14 after the insertion of the second dilator member 37 into the narrow portion 44 is completed, the movable handle portion 14 returns to the initial position by the action of the leaf spring portion 24. At this time, the linear motion of the movable handle portion 14 in the vicinity of the rotation axis 32 is converted by the conversion mechanism.(cam mechanism) 43, and the cylinder 16 rotates 120° in the clockwise direction.

Figure 7:
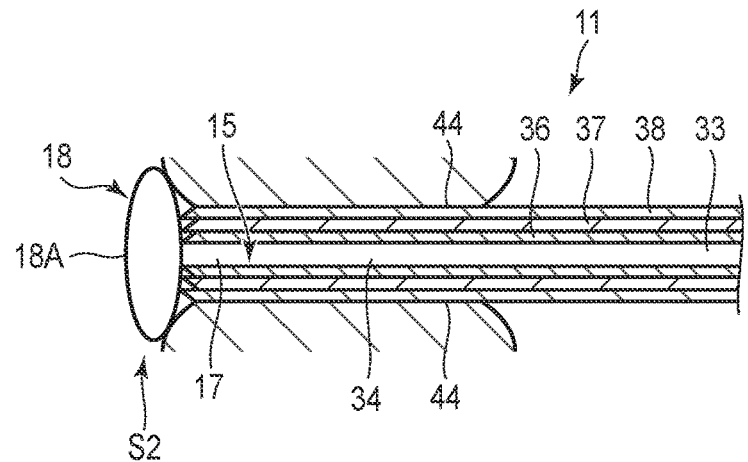
FIG. 7 is a cross-sectional view showing a state after all of the first to third dilator members in the treatment system shown in FIG. 6 have been inserted into a narrow portion.

When the operator grasps the movable handle 14 to release the third spring member 27 from the compressed state, the repulsive force of the third spring member 27 is caused to act on the third dilator member 38. As a result, the third dilator member 38 moves forward from the proximal end portion 33 to the distal end portion 17 and is inserted into the narrow portion 44 and outside the second dilator member 37, as shown in FIG. 7. By inserting the third dilator member 38 into the narrow portion 44, the diameter (inner diameter) of the narrow portion 44 is further increased. At this time, similarly, a reaction force is generated in the direction opposite to the direction in which the second dilator member 37 moves forward; however, the reaction force can be received by the holding portion 18 (balloon-shaped member 18A) provided in the distal end portion 17 of the guide 15.

Figure 8:
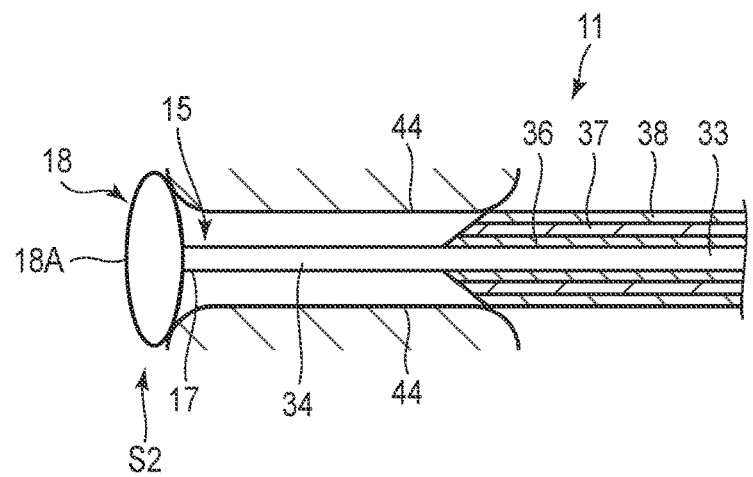
FIG. 8 is a cross-sectional view showing a state after the first to third dilator members have been moved to the proximal end side by a retraction mechanism in the treatment system shown in FIG. 7.
Figure 9:
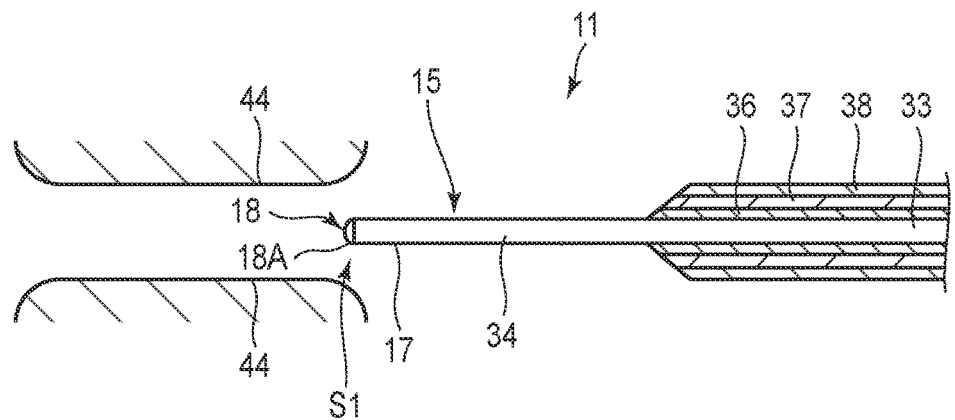
FIG. 9 is a cross-sectional view showing a state after the guide in the treatment system shown in FIG. 8 has been pulled out of the narrow portion.

After the diameter of the narrow portion 44 has been increased, the first to third dilator members 36, 37, and 38 are retracted toward the proximal end portion 33 by a retraction mechanism (not illustrated) as shown in FIG. 8. Then, as shown in FIG. 9, the fluid such as air or water is recovered from the holding portion 18, the holding portion 18 is changed from the second state S2 to the first state S1, and the operator pulls the fixed handle 13 back to the near side. As a result, the guide 15 can be extracted from the narrow portion 44 such as a paranasal sinus. Thus, the treatment for enlarging the narrow portion 44 is completed.

According to the first embodiment, the following is apparent.

The treatment system 11 includes the guide 15 linearly extending from the proximal end portion 33 to the distal end portion 17 and inserted into the narrow portion 44. The tubular dilator members 36, 37, and 38 pass the guide 15 inside and are configured to move forward along the guide 15. The operation portion 20 is configured to move the plurality of dilator members 36, 37, and 38 from the side of the proximal end portion 33 to the side of the distal end portion 17 and to insert the plurality of dilator members 36, 37, and 38 into the narrow portion 44. The holding portion 18 is provided on the guide 15 and is configured to hold the position of the guide 15 with respect to the narrow portion 44.

According to this configuration, the reaction force generated when the dilator members 36, 37, and 38 are inserted into the narrow portion 44 can be received by the holding portion 18. Therefore, it is possible to prevent the guide 15 from retracting due to the reaction force when the dilator members are to be moved forward. Thus, it is possible to prevent a problem wherein the treatment for enlarging the narrow portion 44 cannot be performed properly.

Each of the plurality of dilator members has a tapered portion that tapers toward the distal end portion 17. According to this configuration, the dilator members can be smoothly inserted into the narrow portion 44.

The holding portion 18 generates a holding force for holding the guide 15 at that position against a reaction force when the dilator members are inserted into the narrow portion 44. According to this configuration, the holding portion 18 is not influenced by the reaction force generated when the dilator members are inserted into the narrow portion 44, and the guide 15 can be prevented from retracting due to the reaction force when the dilator members are moved forward.

The holding portion 18 includes the distal end engagement portion provided on the side of the distal end portion 17 of the guide 15. The distal end engagement portion can change its diameter (distance between outer edges) between the first state S1 having a diameter (distance between outer edges) equivalent to the diameter of the narrow portion 44 and the second state S2 in which the distal end engagement portion can be engaged with the inner side of the narrow portion 44 by increasing its diameter from the first state S1. According to this configuration, the holding portion 18 in the second state S2 can prevent the guide 15 from retracting from the narrow portion 44 as much as possible.

The distal end engagement portion includes a balloon-shaped member 18A that is inflatable and deflatable between the first state S1 and the second state S2. According to this configuration, the holding portion 18 can be realized with a simple structure.

The plurality of dilator members include the first dilator member 36 provided at a position adjacent to the guide 15 and the second dilator member 37 positioned outside the first dilator member. The operation portion 20 is configured to insert the second dilator member 37 outside the first member 36 into the narrow portion 44 in the state where the first member 36 has been inserted in the narrow portion 44. According to this configuration, a treatment for gradually expanding the narrow portion 44 can be easily realized.

Hereinafter, a modification of the treatment system 11 according to the first embodiment will be described with reference to FIGS. 10 to 17. In the following embodiments, the parts different from the first embodiment will be mainly described, and descriptions of the parts identical to those of the first embodiment will be omitted.

(First Modification)

Figure 10:
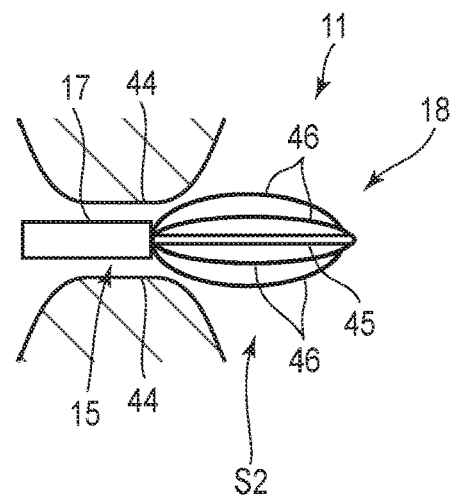
FIG. 10 is a schematic diagram illustrating the holding portion in the first state in the treatment system according to a first modification of the first embodiment.
Figure 11:
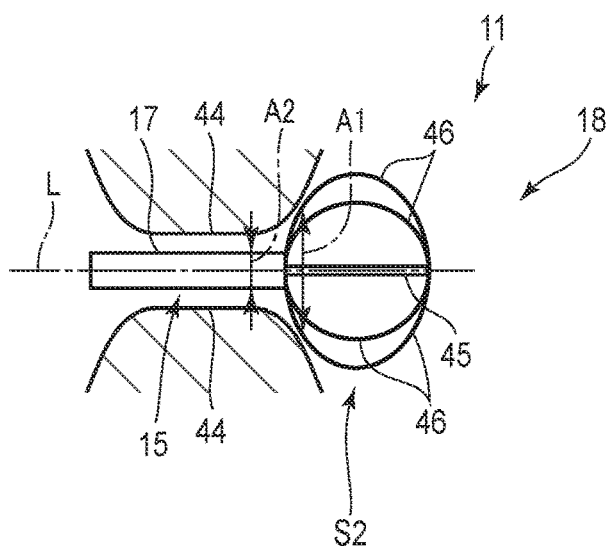
FIG. 11 is a schematic diagram illustrating a state in which the diameter of the holding portion illustrated in FIG. 10 is increased to the second state.

A first modification of the first embodiment will be described with reference to FIGS. 10 and 11.

In the first modification, the configuration of the holding portion 18 (distal end engagement portion) is different from that of the first embodiment. The guide 15 is, for example, tubular. The holding portion 18 includes a shaft 45 configured to be inserted into and removed from the distal end portion 17 of the guide 15, and a plurality of arc-shaped wires 46 that are connected between the distal end of the shaft 45 and the end of the main body 12. The shaft 45 is configured to move forward and backward with respect to the guide 15 by a known mechanism (second operation portion). In the present modification, by pulling the shaft 45 into the distal end portion 17 of the guide 15, the wires 46 can be deformed from a first state S1 in which the plurality of wires 46 are closed to the second state S2 in which the plurality of wires 46 are unfolded to form a larger diameter than the first state S1. The distance between the outer edges of the wires 46 orthogonal to the longitudinal axis L of the guide 15, indicated by the reference symbol A1 in FIG. 11, is greater than the distance between the outer edges of the distal end portions 17 of the guide 15, indicated by the reference symbol A2 in FIG. 11. By setting the plurality of wires 46 to the second state S2, the plurality of wires 46 can be engaged with a deep portion beyond the narrow portion 44. Accordingly, the same effect as in the first embodiment can be obtained.

(Second Modification)

Figure 12:
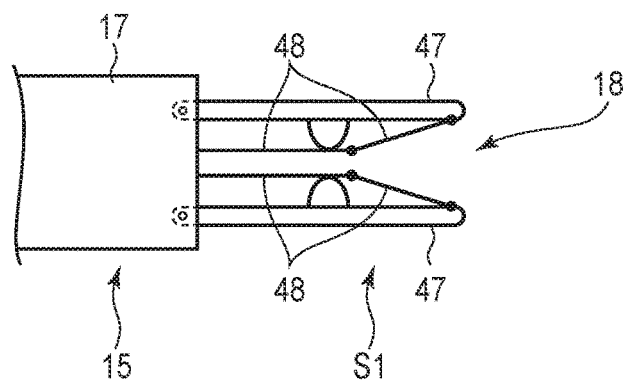
FIG. 12 is a schematic diagram illustrating the holding portion in the first state in the treatment system according to a second modification of the first embodiment.
Figure 13:
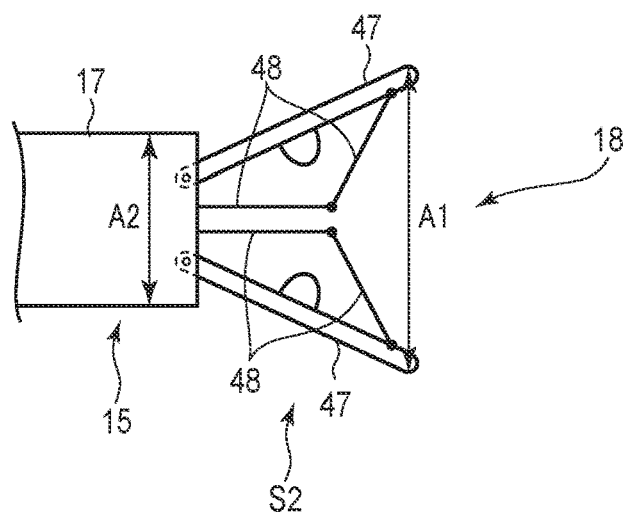
FIG. 13 is a schematic diagram illustrating a state in which the diameter of the holding portion illustrated in FIG. 12 is increased to the second state.

A second modification of the first embodiment will be described with reference to FIGS. 12 and 13.

In the second modification, the configuration of the holding portion 18 (distal end engagement portion) is different from that of the first embodiment. The guide 15 is, for example, tubular. The holding portion 18 includes a pair of pivot plates 47 pivotable around the distal end portion 17 of the guide 15, and a link mechanism 48 configured to pivot the pair of pivot plates 47 in the direction of increasing the distance between the plates. The link mechanism 48 is configured to move forward and backward with respect to the distal end portion 17 of the guide 15 by a known mechanism (second operation portion), and to project from and retract into the distal end portion 17 of the guide 15.

In the present modification, when the link mechanism 48 is projected from the distal end portion 17 of the guide 15, the pair of pivot plates 47 can be pivoted from the first state S1 (closed position) to the second state S2 in which the distance is larger than that in the first state S1. By setting the pair of pivot plates 47 to the second state S2, the pair of pivot plates 47 can be engaged with a deep portion beyond the narrow portion 44. The distance between the outer edges of the pivot plates 47 orthogonal to the longitudinal axis L of the guide 15, indicated by the reference symbol A1 in FIG. 13, is greater than the distance between the outer edges of the distal end portion 17 of the guide 15, indicated by the reference symbol A2 in FIG. 13. Accordingly, the same effect as in the first embodiment can be obtained.

(Third Modification)

A third modification of the first embodiment will be described with reference to FIGS. 14 and 15.

In the third modification, the configuration of the holding portion 18 (distal end engagement portion) is different from that of the first embodiment. The guide 15 is, for example, tubular. The holding portion 18 includes a pair of pivot plates 47 pivotable around the distal end portion 17 of the guide 15, and a push rod 51 configured to project from and retract into the distal end portion 17 of the guide 15. The push rod 51 is configured to move forward and backward with respect to the distal end portion 17 of the guide 15 by a known mechanism (second operation portion). A tip 52 of the push rod 51 can abut thick parts 47A of the pivot plates 47, and the distance between the distal ends of the pivot plates 47 can be increased by moving the push rod 51 forward (projecting the push rod 51 out of the main body 12).

In the present modification, when the push rod 51 is projected from the guide 15, the pair of pivot plates 47 can be pivoted from the first state S1 (closed position) to the second state S2 in which the distance between the distal ends of the pivot plates is larger than that in the first state S1. By setting the pair of pivot plates 47 to the second state S2, the pair of pivot plates 47 can be engaged with a deep portion beyond the narrow portion 44. The distance between the outer edges of the pivot plates 47 orthogonal to the longitudinal axis L of the guide 15, indicated by the reference symbol A1 in FIG. 15, is greater than the distance between the outer edges of the distal end portion 17 of the guide 15, indicated by the reference symbol A2 in FIG. 15. Accordingly, the same effect as in the first embodiment can be obtained.

(Fourth Modification)

Figure 17:
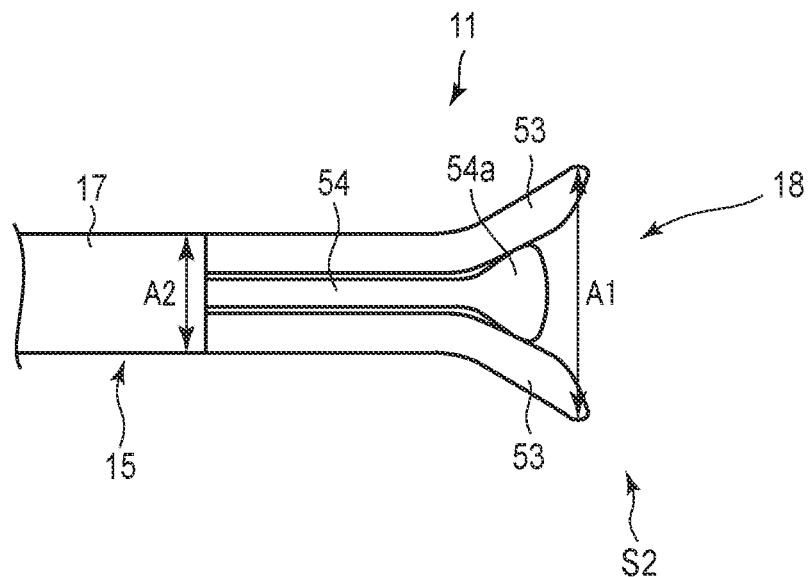
FIG. 17 is a schematic diagram illustrating a state in which the diameter of the holding portion illustrated in FIG. 16 is increased to the second state.

A fourth modification of the first embodiment will be described with reference to FIGS. 16 and 17.

In the fourth modification, the configuration of the holding portion 18 (distal end engagement portion) is different from that of the first embodiment. The guide 15 is, for example, tubular. The holding portion 18 includes a pair of elastic plates 53 having elasticity and fixed to the distal end portion 17 of the guide 15, and a pull rod 54 configured to project from and retract into the distal end portion 17 of the guide 15. In a distal end portion 54a of the pull rod 54, a distance between the outer edges of a cross section intersecting a direction from the proximal end toward the distal end of the guide 15 is larger than a distance between inner edges of the elastic plates 53 at the distal end portion 17 of the guide 15. The pull rod 54 is configured to move forward and backward with respect to the main body 12 by a known mechanism (second operation portion).

In the present modification, when the pull rod 54 is retracted in the direction of being housed in the guide 15, the pair of elastic plates 53 can be deformed from the first state S1 (closed position) to the second state S2 in which the distance between the elastic plates 53 is larger than that in the first state S1. By setting the pair of elastic plates 53 to the second state S2, the pair of elastic plates 53 can be engaged with a deep portion beyond the narrow portion 44. The distance between the outer edges of the elastic plates 53 orthogonal to the longitudinal axis L of the guide 15, indicated by the reference symbol A1 in FIG. 17, is greater than the distance between the outer edges of the distal end portion 17 of the guide 15, indicated by the reference symbol A2 in FIG. 17. Accordingly, the same effect as in the first embodiment can be obtained.

Second Embodiment

Figure 18:
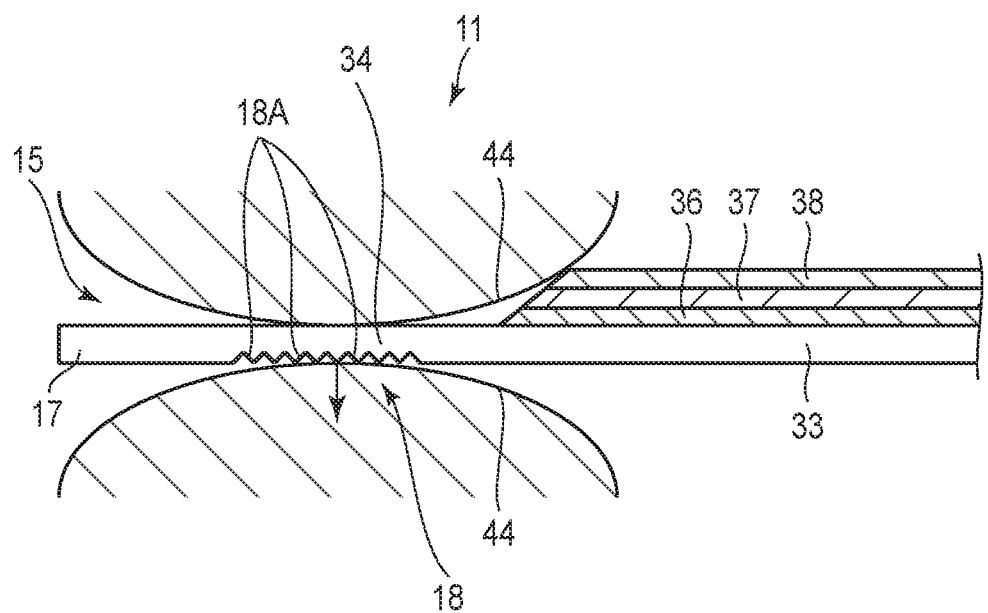
FIG. 18 is a cross-sectional view showing a configuration of a guide, first to third dilator members, and a holding portion in a treatment system according to a second embodiment.

A treatment system 11 according to a second embodiment will be described with reference to FIG. 18. In the second embodiment, the configurations of first to third dilator members 36, 37, and 38 and the configuration of a holding portion 18 are different from those of the first embodiment, but the other parts are the same as those of the first embodiment. Hereinafter, portions different from the first embodiment will be mainly described, and illustration or description of portions that are the same as those of the first embodiment will be omitted.

Unlike the first embodiment, the first to third dilator members 36, 37, and 38 are each formed in a semi-cylindrical shape. One 180° portion around the guide 15 is covered with first to third dilator members 36, 37, and 38, whereas the other 180° portion on the opposite side of the guide 15 is exposed. The first to third dilator members 36, 37, and 38 have the same configuration as that of the first embodiment, except that they are formed in a semi-cylindrical shape.

In the present embodiment, the holding portion 18 is configured as an intermediate engagement portion provided at an intermediate portion 34 (a position between the distal end portion 17 and the proximal end portion 33) of the guide 15. The holding portion 18 (intermediate engagement portion) comprises a plurality of irregularities (concavities and convexities) 18A. The plurality of irregularities 18A are preferably formed, for example, in a knurled shape. As shown in FIG. 18, the holding portion 18 is biased in a direction of pressing against a narrow portion 44 as shown by an arrow, so that the holding portion 18 can bite into the inner surface of the narrow portion 44. As a result, the holding portion 18 can be engaged with the inner surface of the narrow portion 44. The plurality of irregularities 18A are formed only in an angle range of 180° around a longitudinal axis L on the side where the first to third dilator members 36, 37, and 38 are not provided. Therefore, the first to third dilator members 36, 37, and 38 do not interfere with the plurality of irregularities 18A.

Subsequently, with reference to FIG. 18, a treatment for enlarging the narrow portion 44 using the treatment system 11 of the present embodiment will be described. As shown in FIG. 18, the operator inserts the guide 15 into the narrow portion 44 of a human body, for example, a paranasal sinus or the like. The operator inserts the guide 15 through the external naris and positions the guide 15 in the paranasal sinus, for example in the frontal sinus or maxillary sinus. At this time, the guide 15 is inserted into the narrow portion 44 until the distal end portion 17 of the guide 15 is positioned deeper than the narrow portion 44.

The operator biases the guide 15 so as to press the holding portion 18 (the intermediate engagement portion) against the inner surface of the narrow portion 44. As a result, the holding portion 18 is engaged with the inner surface of the narrow portion 44. Accordingly, the position of the guide 15 can be fixed with respect to the narrow portion 44 so that the guide 15 does not retract. In this state, by grasping the movable handle portion 14, the operator inserts the first dilator member 36, the second dilator member 37, and the third dilator member 38 into the narrow portion 44 in this order by the repulsive forces of the first to third spring members 25, 26, and 27, as in the above-described embodiment. By inserting the first to third dilator members 36, 37, and 38 into the narrow portion 44, the diameter (inner diameter) of the narrow portion 44 is gradually increased.

After the diameter of the narrow portion 44 has been increased, the first to third dilator members 36, 37, and 38 are retracted toward the proximal end portion 33 by a retraction mechanism (not shown). Then, the biasing of the holding portion 18 onto the inner surface of the narrow portion 44 (the biasing in the direction of the arrow in FIG. 18) is released, and the operator pulls back the fixed handle portion 13 toward the operator side, whereby the guide 15 can be extracted out of the narrow portion 44 such as the paranasal sinuses. Thus, the treatment for enlarging the narrow portion 44 is completed.

According to the second embodiment, the holding portion 18 is the intermediate engagement portion provided at a position between the distal end portion 17 and the proximal end portion 33 of the guide 15. The intermediate engagement portion is engageable with the inner surface of the narrow portion 44. According to this configuration, it is possible to prevent the guide 15 from retracting from the narrow portion 44 by the intermediate engagement portion as much as possible.

The intermediate engagement portion is a plurality of irregularities 18A configured to be engaged with the inner surface of the narrow portion 44. According to this configuration, the guide 15 can be fixed to the inner surface of the narrow portion 44 by a simple technique of pressing the intermediate engagement portion formed of the irregularities 18A against the inner surface of the narrow portion 44. Thus, when the dilator members are moved forward, it is possible to prevent the guide 15 from moving backward due to the reaction force as much as possible.

Figure 19:
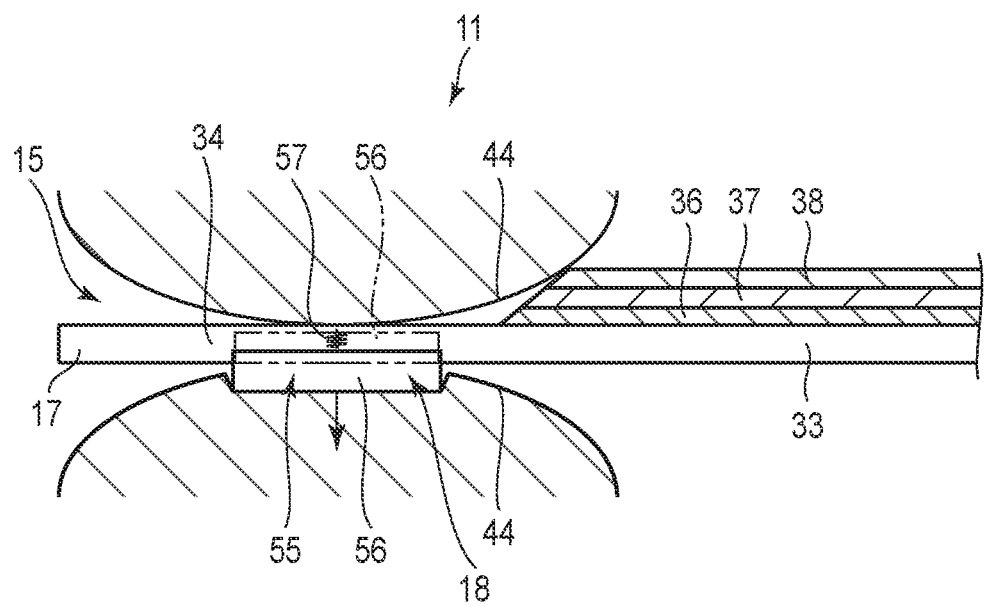
FIG. 19 is a cross-sectional view showing a guide, first to third dilator members, and a holding portion (movable piece) of a treatment system according to a first modification of the second embodiment.
Figure 20:
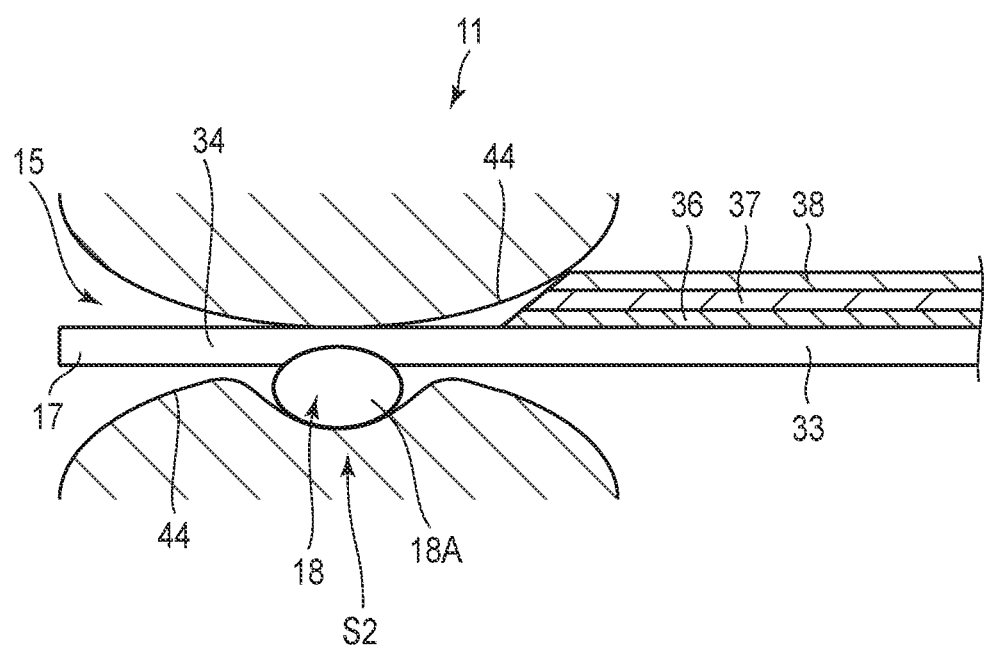
FIG. 20 is a cross-sectional view showing a guide, first to third dilator members, and a holding portion (balloon-shaped member) of a treatment system according to a second modification of the second embodiment.

Hereinafter, a modification of the treatment system 11 of the second embodiment will be described with reference to FIGS. 19 and 20. In the following embodiments, the parts different from the second embodiment will be mainly described, and descriptions of the parts identical to those of the second embodiment will be omitted.

(First Modification)

A first modification of the second embodiment will be described with reference to FIG. 19.

In the first modification, the configuration of the holding portion 18 (intermediate engagement portion) is different from that of the second embodiment. The holding portion 18 comprises a movable piece 55 configured to be housed inside the guide 15 or to protrude outward from the outer peripheral surface of the guide 15. The movable piece 55 is formed in an angle range of 180° around the longitudinal axis L on the side where the first to third dilator members 36, 37, and 38 are not provided. Therefore, the first to third dilator members 36, 37, and 38 do not interfere with the movable piece 55.

The movable piece 55 includes a button portion 56 and a spring 57 for biasing the button portion 56 outward in the radial direction of the guide 15. The button portion 56 is configured to move back and forth by the action of the spring 57 between a protruding position indicated by a solid line in FIG. 19 and a retracted position indicated by a two-dot chain line. The movable piece 55 can be engaged with the narrow portion 44 by moving to the protruding position and being pressed into the inner surface of the narrow portion 44 in the state of having entered the narrow portion 44. Accordingly, the same effect as in the first embodiment can be obtained.

(Second Modification)

A second modification of the second embodiment will be described with reference to FIG. 20.

In the second modification, the configuration of the holding portion (intermediate engagement portion) is different from that of the second embodiment. The holding portion 18 (intermediate engagement portion) comprises a balloon-shaped member 18A having a directivity in the inflation direction so as to inflate only in an angular range of 180° around the longitudinal axis L on the side where the first to third dilator members 36, 37, and 38 are not provided on the entire circumference of the guide 15. Therefore, the first to third dilator members 36, 37, and 38 do not interfere with the balloon-shaped member 18A.

The balloon-shaped member 18A comprises a balloon formed of a rubbery elastic material, and is inflatable and contractible. The balloon-shaped member 18A can be suitably formed of a rubber material or the like. The balloon-shaped member 18A can be deformed between a first state S1 having a diameter (distance between outer edges in a direction intersecting the longitudinal axis direction) equivalent to the diameter (inner diameter) of the narrow portion 44 of a paranasal sinus, and a second state S2 having a larger diameter (distance between outer edges) than the first state S1. The balloon-shaped member 18A is inflated from the first state S1 to the second state S2 in the state where the balloon-shaped member 18A has entered the narrow portion 44, so that the balloon-shaped member 18A can be engaged with the narrow portion 44 by being sunk into the inner surface of the narrow portion 44. Accordingly, the same effect as in the first embodiment can be obtained.

Third Embodiment

A treatment system 11 according to a third embodiment will be described with reference to FIGS. 21 and 22. In the third embodiment, the configuration of a holding portion 18 is different from that of the first embodiment, but the other parts are the same as those of the first embodiment. Hereinafter, portions different from the first embodiment will be mainly described, and illustration or description of portions that are the same as those of the first embodiment will be omitted.

The holding portion 18 is formed in a cylindrical shape, and is provided around first to third dilator members 36, 37, and 38. For this reason, the holding portion 18 covers the periphery of the first to third dilator members 36, 37, and 38. A side of a distal end portion 33 of the holding portion 18 is fixed to the guide 15. An abutting portion 18A (abutting surface) that is inclined (tapered) so as to decrease in thickness toward the distal end portion 17 of the guide 15 is formed at the distal end of the holding portion 18. It is preferable that the abutting portion 18A (abutting surface) be flush with the surface formed by the distal ends of the first to third dilator members 36, 37, and 38. The holding portion 18 can abut on a proximal side of an entrance of the narrow portion 44 at the abutting portion 18A.

Subsequently, with reference to FIGS. 21 and 22, a treatment for enlarging the narrow portion 44 using the treatment system of the present embodiment will be described. The operator inserts the guide 15 into a narrow portion 44 of the human body, for example into a paranasal sinus or the like. The operator inserts the guide 15 through the external naris and positions the guide 15 in the paranasal sinus, for example in the frontal sinus or maxillary sinus. At this time, as shown in FIG. 21, the guide 15 is inserted until the distal end portion 17 of the guide 15 is positioned deeper than the narrow portion 44.

The operator biases the movable handle portion 14 in a direction approaching the patient. As shown in FIG. 21, the abutting portion 18A of the holding portion 18 is brought into contact with a position on the proximal side of the entrance of the narrow portion 44. The operator maintains a biased state of the movable handle portion 14, whereby the position of the guide 15 can be fixed with respect to the narrow portion 44 so that the guide 15 does not retract. In this state, by grasping the movable handle portion 14, as shown in FIG. 22, the operator inserts the first dilator member 36, the second dilator member 37, and the third dilator member 38 into the narrow portion 44 in this order by the repulsive forces of the first to third spring members 25, 26, and 27, as in the above-described embodiments. By inserting the first to third dilator members 36, 37, and 38 into the narrow portion 44, the diameter (inner diameter) of the narrow portion 44 is gradually increased. At this time, when the first to third dilator members 36, 37, and 38 move forward, a reaction force acts on the guide 15. However, even in this case, since the holding portion 18 is pressed against the narrow portion 44 via the abutting portion 18A, the guide 15 is prevented from retracting due to the reaction force.

After the diameter of the narrow portion 44 has been increased, the first to third dilator members 36, 37, and 38 are retracted toward the proximal end portion 33 by a retraction mechanism (not shown). Then, the biasing of the holding portion 18 onto the proximal side of the entrance of the narrow portion 44 is released, and the operator pulls back the fixed handle portion 13 toward the operator side, whereby the guide 15 can be extracted out of the narrow portion 44 such as the paranasal sinuses. Thus, the treatment for enlarging the narrow portion 44 is completed.

According to the third embodiment, the holding portion 18 includes the abutting portion 18A configured to be brought into contact with a position on the proximal side of the entrance of the narrow portion 44. According to this configuration, the position of the guide 15 with respect to the narrow portion 44 can be fixed by the holding portion 18. Thus, the reaction force generated when the dilator members are inserted into the narrow portion 44 can be received by the holding portion 18, and the guide 15 can be prevented from retracting due to the reaction force when the dilator members are to be moved forward. Thus, it is possible to prevent a situation where the treatment for enlarging the narrow portion 44 cannot be performed.

In this third embodiment, the abutting portion 18A of the holding portion 18 is brought into contact with a position on the proximal side of the entrance of the narrow portion 44, but the position where the abutting portion 18A is brought into contact is not limited to this. The position of the guide 15 may be maintained by bringing the abutting portion 18A around the entrance of the nasal cavity (external naris) or the like.

Fourth Embodiment

Figure 23:
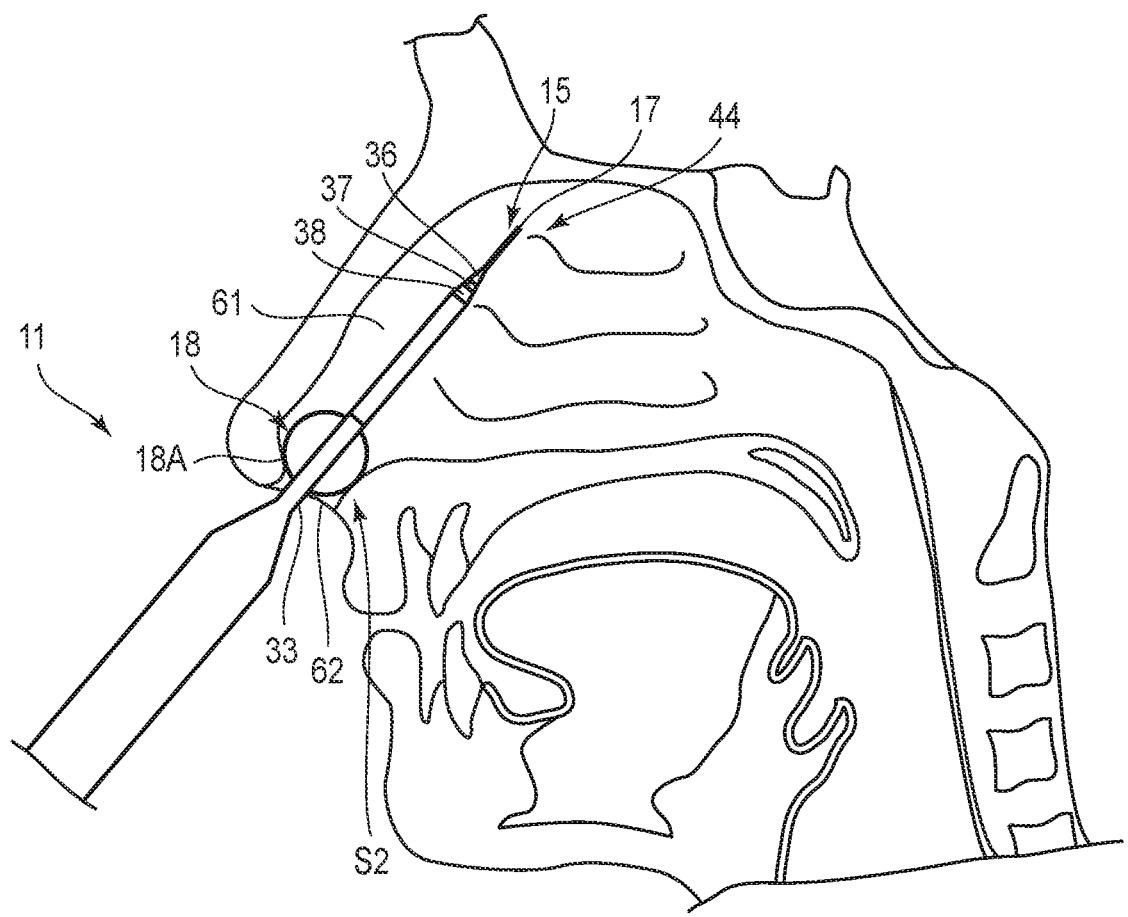
FIG. 23 is a cross-sectional view showing a configuration of a guide, first to third dilator members, and a holding portion in a treatment system according to a fourth embodiment.

A treatment system 11 according to a fourth embodiment will be described with reference to FIG. 23. In the fourth embodiment, the configuration of a holding portion 18 is different from that of the first embodiment, but the other parts are the same as those of the first embodiment. Hereinafter, portions different from the first embodiment will be mainly described, and illustration or description of portions that are the same as those of the first embodiment will be omitted.

In the present embodiment, the holding portion 18 includes a proximal end engagement portion provided on the side of the proximal end portion 33 of the guide 15. The holding portion 18 (proximal end engagement portion) comprises a balloon-shaped member 18A. The balloon-shaped member 18A comprises a balloon formed of a rubbery elastic material. The balloon-shaped member 18A can be suitably formed of a rubber material or the like. The holding portion 18 can be inflatable and deflatable. The holding portion 18 is located inside a nasal cavity 61 and near an external naris 62 when the guide 15 is inserted into the narrow portion 44 of the paranasal sinus. The holding portion 18 can be deformed between a first state S1 that is a deflated state and a second state S2 having a larger diameter (distance between outer edges) than the first state S1. In the present embodiment, the nasal cavity 61 is an example of a sinus which the holding portion 18 in the second state S2 engages with.

Subsequently, the enlargement treatment of the narrow portion 44 using the treatment system 11 of the present embodiment will be described with reference to FIG. 23. The operator inserts the guide part 15 into a narrow portion 44 of the human body, for example into a paranasal sinus or the like. The operator inserts the guide 15 through the external naris 62 and positions the guide 15 in the paranasal sinus, for example in the frontal sinus or maxillary sinus. At this time, the guide 15 is inserted into the narrow portion 44 until the distal end portion 17 of the guide 15 is positioned deeper than the narrow portion 44.

The operator inflates the holding portion 18 (balloon-shaped member 18A) from the first state S1 to the second state S2 by sending a fluid such as air or water to the holding portion 18. As a result, the holding portion 18 is engaged with the inner wall of the nasal cavity 61 (sinus) near the external naris 62. Accordingly, the position of the guide 15 can be fixed with respect to the narrow portion 44 so that the guide 15 does not retract. In this state, by grasping the movable handle portion 14, the operator inserts the first dilator member 36, the second dilator member 37, and the third dilator member 38 into the narrow portion 44 in this order by the repulsive forces of the first to third spring members 25, 26, and 27, as in the above-described embodiment. By inserting the first to third dilator members 36, 37, and 38 into the narrow portion 44, the diameter (inner diameter) of the narrow portion 44 is gradually increased. At this time, when the first to third dilator members 36, 37, and 38 move forward, a reaction force acts on the guide 15. However, even in this case, since the reaction force can be received by the holding portion 18, the guide 15 is prevented from retracting due to the reaction force.

After the diameter of the narrow portion 44 has been increased, the first to third dilator members 36, 37, and 38 are retracted toward the proximal end portion 33 by a retraction mechanism (not shown). Then, the balloon-like member 18A is contracted from the second state S2 to the first state S1, and the operator pulls back the fixed handle portion 13 toward the operator's side, whereby the guide 15 can be extracted out of the narrow portion such as the paranasal sinuses. Thus, the treatment for enlarging the narrow portion 44 is completed.

According to the present embodiment, the holding portion 18 is a proximal end engagement portion provided on the side of the proximal end portion 33 of the guide 15. The proximal end engagement portion is configured to change the diameter (distance between outer edges) between a first state S1 having a predetermined diameter (distance between outer edges) and a second state S2 in which the diameter is larger than that in the first state S1 and to engage with the inner surface of the sinus on the proximal side of the entrance of the narrow portion 44. According to this configuration, since the reaction force generated when the dilator members are inserted into the narrow portion 44 can be received by the holding portion 18, the guide 15 can be prevented from retracting due to the reaction force when the dilator members are to be moved forward. Thus, it is possible to prevent a situation where the treatment for enlarging the narrow portion 44 cannot be performed.

The proximal end engagement portion is a balloon-shaped member 18A that is inflatable and deflatable between the first state S1 and the second state S2. According to this configuration, the proximal end engagement portion can be realized with a simple structure.

Fifth Embodiment

A treatment system 11 according to a fifth embodiment will be described with reference to FIG. 24. In the fifth embodiment, the configuration of a holding portion 18 is different from that of the first embodiment, but the other parts are the same as those of the first embodiment. Hereinafter, portions different from the first embodiment will be mainly described, and illustration or description of portions that are the same as those of the first embodiment will be omitted.

In the present embodiment, the holding portion 18 is a proximal end engagement portion provided on the side of the proximal end portion 33 of the guide 15. The holding portion 18 (proximal end engagement portion) is formed in an arm shape that supports the main body 12. The holding portion 18 preferably has a plurality of joints so that the position of the guide section 15 can be finely adjusted. The plurality of joints can switch between a free state in which the angle can be freely changed and a restricted state in which the current angle is maintained. Switching between the free state and the restricted state may be realized by, for example, screwing a screw or the like or bringing a brake into contact with a rotating shaft or the like. The holding portion 18 is fixed to a fixed object 63 such as a bed or a chair on which the patient is placed.

Subsequently, with reference to FIG. 24, a treatment for enlarging the narrow portion 44 using the treatment system 11 of the present embodiment will be described. The operator inserts the guide 15 into a narrow portion 44 of the human body, for example into a paranasal sinus or the like. The operator inserts the guide 15 through the external naris 62 and positions the guide 15 in the paranasal sinus, for example in the frontal sinus or maxillary sinus. At this time, the guide 15 is inserted into the narrow portion 44 until the distal end portion 17 of the guide 15 is positioned deeper than the narrow portion 44.

The operator switches each joint of the holding portion 18 from the free state to the restricted state. As a result, the positions of the main body 12 and the guide 15 are fixed. Accordingly, the position of the guide 15 can be fixed with respect to the narrow portion 44 so that the guide 15 does not retract. In this state, by grasping the movable handle portion 14, the operator inserts the first dilator member 36, the second dilator member 37, and the third dilator member 38 into the narrow portion 44 in this order by the repulsive forces of the first to third spring members 25, 26, and 27, as in the above-described embodiment. By inserting the first to third dilator members 36, 37, and 38 into the narrow portion 44, the diameter (inner diameter) of the narrow portion 44 is gradually increased. At this time, when the first to third dilator members 36, 37, and 38 move forward, a reaction force acts on the guide 15. However, even in this case, since the reaction force can be received by the holding portion 18 and the fixed object 63, the guide 15 is prevented from retracting due to the reaction force.

In this state, the first to third dilator members 36, 37, and 38 are retracted toward the proximal end portion 33 by a retraction mechanism (not shown). Then, the joints of the holding portion 18 are released from the restricted state to the free state, and the operator pulls back the fixed handle portion 13 toward the operator side, whereby the guide 15 can be extracted out of the narrow portion 44 such as the paranasal sinuses. Thus, the treatment for enlarging the narrow portion 44 is completed.

According to the present embodiment, the holding portion 18 is a proximal end engagement portion provided on the side of the proximal end portion 33 of the guide 15. The proximal end engagement portion is fixed to the fixed object 63 on which the patient is placed. According to this configuration, the position of the guide 15 can be fixed with respect to the narrow portion 44 by a method of fixing the proximal end engagement portion to a structure outside the body of the patient without fixing the proximal end engagement portion to the body of the patient. Thus, a reaction force generated when the dilator members are inserted into the narrow portion 44 can be received by the holding portion 18, and the guide 15 can be prevented from retracting due to the reaction force when the dilator members are to be moved forward. Thus, it is possible to prevent a situation where the enlargement of the narrow portion 44 cannot be performed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment system comprising:
a guide extending linearly or curvilinearly from a proximal end portion to a distal end portion;
a plurality of tubular dilator members passing the guide inside, the dilator members being configured to move forward along the guide and configured to be inserted into a narrow portion;
an operation portion configured to sequentially move the plurality of dilator members from a side of the proximal end portion to a side of the distal end portion; and
a holding portion provided on the guide, a distance between outer edges of the holding portion in a direction intersecting a direction from the side of the proximal end portion toward the side of the distal end portion of the guide being larger or being configured to be larger than a distance between outer edges of the guide, the holding portion being configured to maintain a position of the guide relative to the narrow portion while the plurality of tubular members are inserted into the narrow portion.

2. The treatment system according to claim 1, wherein each of the dilator members includes a tapered portion tapered toward the distal end portion of the guide.

3. The treatment system according to claim 1, wherein the holding portion is configured to generate a holding force to maintain the guide at a position against a reaction force generated when the dilator members move.

4. The treatment system according to claim 1, wherein:
the holding portion includes a distal end engagement portion provided on the side of the distal end portion of the guide, and
the distal end engagement portion is configured to change the distance between the outer edges of the holding portion between a first state in which the distance between the outer edges of the holding portion is equivalent to a distance between inner walls of the narrow portion and a second state in which the distance between the outer edges of the holding portion is greater than the distance between the outer edges in the first state.

5. The treatment system according to claim 4, wherein the distal end engagement portion is a balloon-shaped member that is configured to inflate and deflate between the first state and the second state.

6. The treatment system according to claim 1, wherein:
the holding portion includes an intermediate engagement portion provided at a position between the distal end portion and the proximal end portion of the guide,
the intermediate engagement portion is configured to engage with an inner surface of the narrow portion.

7. The treatment system according to claim 6, wherein the intermediate engagement portion includes a plurality of irregularities.

8. The treatment system according to claim 1, wherein:
the holding portion includes a proximal end engagement portion provided closer to the side of the proximal end portion than the distal end portion of the guide, and
the proximal end engagement portion is configured to change the distance between the outer edges of the holding portion between a first state having a predetermined diameter and a second state having a larger diameter than the predetermined diameter, and to engage with an inner surface of a sinus on a proximal side of an entrance of the narrow portion.

9. The treatment system according to claim 8, wherein the proximal end engagement portion is a balloon-shaped member that is configured to inflate and deflate between the first state and the second state.

10. The treatment system according to claim 1, wherein the holding portion includes an abutting portion configured to abut on a proximal side of an entrance of the narrow portion.

11. The treatment system according to claim 1, wherein:
the dilator members include:
a first member adjacent to the guide; and
a second member located outside the first member, and
the operation portion is configured to insert the second member into the narrow portion outside the first member, while the first member is inserted into the narrow portion.

12. The treatment system according to claim 1, wherein the dilator members are configured to be inserted into a boundary between a nasal cavity and a paranasal sinus which is located in a deeper portion than the nasal cavity.

13. The treatment system according to claim 1, wherein:
the operation portion includes a handle portion which is grasped, and
the dilator members are configured to sequentially move forward and to be inserted into the narrow portion in accordance with an operation of the handle portion.

14. The treatment system according to claim 1, wherein:
the operation portion includes a plurality of elastic members provided on a proximal end side of the respective dilator members, and
the dilator members are configured to sequentially advanced toward the narrow portion by repulsive forces of the elastic members and are sequentially inserted into the narrow portion when the plurality of elastic members are sequentially released in response to the operation of the operation portion.

15. The treatment system according to claim 14, wherein:
the operation portion includes a cylinder configured to rotate about a rotation axis, and
the plurality elastic members are provided on the cylinder, the plurality of elastic members being configured to be sequentially released by the rotation of the cylinder.

16. The treatment system according to claim 15, wherein:
the operation portion includes a conversion mechanism configured to rotate the cylinder, and
the cylinder is configured to rotate in response to operation of the operation portion by the conversion mechanism.

17. The treatment system according to claim 14, wherein each of the plurality of elastic members is a spring.

18. A treatment system comprising:
a guide extending linearly or curvilinearly from a proximal end portion to a distal end portion;
a plurality of tubular dilator members passing the guide inside, the dilator members being configured to move forward along the guide and configured to be inserted into a narrow portion;
an operation portion configured to sequentially move the plurality of dilator members from a side of the proximal end portion to a side of the distal end portion; and
a holding portion, wherein:
the holding portion includes a proximal end engagement portion provided on the side of the proximal end portion of the guide, and
the proximal end engagement portion is configured to be fixed to a fixed object on which a patient is placed.

19. A method for enlarging a narrow portion using a plurality of tubular dilator members passing a guide which extends linearly from a proximal end portion to a distal end portion and configured to move forward along the guide, the method comprising:
inserting the guide into the narrow portion;
fixing a position of the guide relative to the narrow portion by a holding portion provided on the guide; and
concurrently with the fixing, sequentially moving the dilator members forward along the guide toward the narrow portion to enlarge the narrow portion.

20. The method according to claim 19, wherein the sequentially moving the dilator members comprises sequentially inserting the dilator members in an order from an inner dilator member closest to the guide member to an outer dilator member away from the guide to enlarge the narrow portion in response to operation of the operation portion.

* * * * *